US006830929B1

(12) United States Patent
Sandalon et al.

(10) Patent No.: US 6,830,929 B1
(45) Date of Patent: Dec. 14, 2004

(54) IN VITRO CONSTRUCTION OF SV40 VIRUSES AND PSEUDOVIRUSES

(75) Inventors: Ziv Sandalon, Petach Tikva (IL); Amos Oppenheim, Jerusalem (IL); Ariella Oppenheim, Jerusalem (IL)

(73) Assignees: Yissum Research Development Company of the Hebrew University, Jerusalem (IL); Hadasit Medical Research Services and Development Company, Jerusalem (IL)

(*) Notice: Subject to any disclaimer, the term of this patent is extended or adjusted under 35 U.S.C. 154(b) by 0 days.

(21) Appl. No.: 09/068,293

(22) PCT Filed: Nov. 6, 1996

(86) PCT No.: PCT/IL96/00143

§ 371 (c)(1),
(2), (4) Date: May 6, 1998

(87) PCT Pub. No.: WO97/17456

PCT Pub. Date: May 15, 1997

(30) Foreign Application Priority Data

Nov. 6, 1995 (IL) ................................................ 115880

(51) Int. Cl.$^7$ ........................ C12N 15/86; C12N 15/63; C12N 5/10; C12N 15/64

(52) U.S. Cl. ................. 435/455; 435/235.1; 435/320.1; 435/69.1; 435/325; 435/368; 435/372; 435/236; 435/239; 435/456; 536/23.1; 536/24.1; 536/24.5; 530/350

(58) Field of Search ........................... 435/235.1, 320.1, 435/69.1, 325, 368, 372, 236, 239, 455, 456, 6; 536/23.1, 24.1, 24.5; 530/350; 424/93.1, 93.2, 93.6; 514/2, 44

(56) References Cited

U.S. PATENT DOCUMENTS 5,863,541 A * 1/1999 Samulski et al. ......... 424/192.1
6,107,062 A * 8/2000 Hu et al. .................. 435/91.41

FOREIGN PATENT DOCUMENTS

WO      WO 92/16638    * 10/1992 ................. 435/461

OTHER PUBLICATIONS

Hong et al. Protection from proteolysis using a T4:T7–RNAP phage expression–packaging–processing system. Gene vol. 162(1):5–11, 1995.*
Colomar et al. Opening and refolding of simian virus 40 and in vitro packaging of foreigh DNA. J. Virol. vol. 67:2779–2786, May 1993.*
Orkin et al. Report and recommendations of the panel to assess the NIH investment in research on gene therapy, Dec. 1995.*
Verma et al. Gene therapy—promises, problems and prospects. Nature. vol. 389:239–242, Sep. 1997.*

Marshall, E. Gene therapy's growing pains. Science. vol. 269:1050–1055, Aug. 1995.*
Anderson, WF Human gene therapy. Nature. vol. 392:25–30, Aug. 1998.*
Christensen, M. & Rachmeler, M.; Studies on the In Vitro Formation of Infectious DNA–Protein Aggregates from SV40 Components (1976) *Virology* 75:433–41.
Colomar, M.C., et al., Openig and Refolding of Simian Virus 40 and In Vitro Packaging of Foreign DNA (1993) *J. Virol.* 67:2779–2788.
Forstova, J., et al., Polyoma Virus Pseudocapsids as Efficient Carriers of Heterologous DNA into Mammalian Cells (1995) *Hum. Gene Therapy* 6:297–306.
Tooze, J. (1981) DNA Tumor Viruses.; Lytic Cycle of SV40 and Polyoma Virus, Cold Spring Harbor Laboratory, Cold Spring Harbor, New York.
Liddington, R., et al. Structure of Simian Virus 40 at 3.8–Å resolution. (1991) Nature 354:278–284.
Resnick, J & Shenk, T.; Simian Virus 40 Agnoprotein Facilitates Normal Nuclear Location of the Major Capsid Polypeptide and Cell to Cell Spread of Virus. (1986) J. Virol. 60:1098–1106.
Ng, S.C., et al.; Simian Virus 40 Maturation in Cells Harboring Mutants Delected in the Agnogene. (1985) *J. Biol. Chem.* 260:1127–1132.
Carswell, S.& Alwine, J. C.; Simian Virus 40 Agnoprotein Facilitates Perinuclear–Nuclear Localization of VP1, the Major Capsid Protein. (1986) *J. Virol.* 60:1055–1061.
Garber, E.A., et al.; Intracellular SV40 Nucleoprotein Complexes: Synthesis to Encapsidation. (1980) *Virology* 107: 389–401.
Bina, M.; Simian Virus 40 Asembly. (1986) *Comments Mol. Cell Biophys.* 4:55–62.
Soussi, T.; DNA–Binding Properties of the Major Structural Protein of Simian Virus 40. (1986) *J. Virol.* 59:740–742.
Clever, J., et al.; Identification of a DNA Binding Domain in Simian Virus 40 Capsid Proteins VP2 and VP3. (1993) *J. Biol. Chem.* 268:20877–20883.

(List continued on next page.)

*Primary Examiner*—David Guzo
(74) *Attorney, Agent, or Firm*—John P. White; Cooper & Dunham LLP

(57) ABSTRACT

The invention relates to constructs capable of infecting mammalian cells comprising at least one semi-purified or pure SV40 capsid protein and a constituent selected from the group consisting of an exogenous DNA, a vector comprising an exogenous DNA, an exogenous RNA, a vector comprising an exogenous RNA, an exogenous protein or peptide product, and antisense RNA, ribozyme RNA or any RNA or DNA which inhibits or prevents the expression of undesired protein(s) in the mammalian cell and optionally further comprising operatively linked regulatory elements sufficient for the expression and/or replication of the exogenous protein in a mammalian cell. The invention further relates to a method for the in vitro construction of SV40 virus or pseudovirus constructs according to the invention.

42 Claims, 6 Drawing Sheets

OTHER PUBLICATIONS

Oppenheim, A., et al.; Efficient Introduction Of Plasmid DNA into Human Hemopoietic Cells by Encapsidation in Simian Virus 40 Pseudovirions. (1986) *Proc. Natl. Acad. Sci. USA* 83:6925–6929.

Oppenheim, A., et al.; A cis–Acting DNA Signal for Encapsidation of Simian Virus 40. (1992) *J. Virol.* 66:5320–5328.

Oppenheim, A., et al.; Dynamics of the Nucleoprotein Structure of Simian Virus 40 Regulatory Region During Viral Development. (1994). *J. Mol. Biol.* 238:501–513.

Dalyot–Herman, N. et al.; The Simian Virus 40 Packaging Signal ses is Composed of Redundant DNA elements which are Partly Interchangeable. (1996) *J. Mol. Biol.* 259:69–80.

Oppenheim A., et al.; Efficient Introduction and Transient Expression of Exogenous Genes in Human Hemopoietic Cells. (1987) *Ann. New York Acad. Sci.* 511:418–427.

Dalyot, N. & Oppenheim, A. (1989) Efficient transfer of the complete human beta–globin gene into human and mouse hemopoietic cells via SV40 pseudovirions. In: Gene Transfer and Gene Therapy (Beaudet, A.L., Mulligan R., I.M. Verma, eds), pp. 47–56, Alan R. Liss, Inc., New York.

Oppenheim, A., et al. (1992) Development of somatic gene therapy: A simian virus 40 pseudoviral vector for hemopoietic cells. In Genetic Among Jews (Bonne–Tamir, B., A. Adams, eds), pp. 365–375, Oxford University Press, Oxford.

Schreiber, E., et al; Rapid Detection of Octamer Binding Proteins with 'mini–extracts', Prepared From a Small Number of Cells. (1989) *Nucl. Acids Res.* 15:6419.

Sandalon, Z. et al.; In Vitro Assembly of SV40 Virions and Pseudovirions: Vector Development for Gene Therapy. (1997) *Human Gene Therapy* 8:843–849.

Szczylik, C. et al; Selective Inhibition of Leukemia Cell Proliferation by BCR–ABL Antisense Oligodeoxynucleotides. (1991). *Science*, 253:562–565.

Garcia–Hernandaz, B. & Sanchez–Garcia, I.; Retroviral Vector Design for Gene Therapy of Cancer: Specific Inhibition and Tagging of BCR–ABL$^{P190}$ Cells (1996) *Mol. Medicine*, 2: 125–133.

Oppenheim, A. & Peleg, A..; Helpers for Efficient Encapsidation of SV40 Pseudovirions. (1989) *Gene* 77:79–86.

fSmith, D.B. & Johnson, K.S.; Single Step Purifictaion of Polypeptides Expressed in *Escherichia coli* as Fusions with Glutathione S–Transferase (1988) *Gene* 67:31–40.

Luckow, V.A. & Summers, M.D.; Trends in the Development of Baculovirus Expression Vectors. (1988) *Biotechnology* 6:47–55.

Luckow, V.A. & Summers, M.D.; High Level Expression of Nonfused Foreigh Genes with *Autographa Californica* Nuclear Polyhedrosis Virus Expression Vectors. (1989) *Virology* 170:31–39.

Summers, M.D. & Smith, G.E. (1988) A manual of methods for baculovirus vecotrs and insect cell culture procedures. Texas Agricultural Experiment Station, College Station, Texas.

Laemmli, U.K.; Clevage of Structural Proteins During the Assembly of the Head of Bacteriophage T4. (1970) *Nature* 277:680–685.

Harlow, E. & Lane, D. (1988) Antibodies, a laboratory manual. Cold Spring Harbor Laboratory, N.Y., Cold Spring Harbor.

Sedman, S.A., et al.; Leader–Encoded Open Reading Frames Modulate both the Absolute and Relative Rates of Synthesis of the Virion Proteins of Simian Virus 40. (1989) *J. Virol.* 63:3884–3893.

Sedman, S.A. et al.; Translation Initiation at a Downstream AUG Occurs with Increased Efficiency when the Upstream AUG is Located Very Close to the 5' Cap. (1990) *J. Virol.* 64:453–457.

Gerard, R.D. & Gluzman, Y.; New Host Cell System for Regulated Simian Virus 40 DNA Replication. (1985) *Mol. Cell. Biol.* 5:3231–3240.

Chang, X.B. & Wilson, J.H.; Formation of Deletions after Initiation of Simian Virus 40 Replication: Influence of Packaging Limit of the Capsid. (1986) *J. Virol.* 58:393–401.

Dalyot, N.; Regulation of human globin genes and the development of a model for gene therapy of β–thalassemia, Ph.D. Thesis, (1994) The Hebrew University, Jerusalem.

Martin, R.G.; On the Nucleoprotein Core of Simian Virus 40. (1977) *Virology* 83:433–437.

* cited by examiner

IN VITRO CONSTRUCTION OF SV40 VIRUSES AND PSEUDOVIRUSES

RELATED APPLICATION(S)

This application is the U.S. National Phase of PCT/IL96/00143, filed on Nov. 6, 1996; which claims priority to Israeli Application No.: 115880 filed on Nov. 6, 1995, the entire teachings of which are incorporated herein by reference.

FIELD OF THE INVENTION

The invention relates to methods of in vitro construction of SV40 viruses or pseudoviruses comprising exogenous nucleic acid or exogenous protein or peptide which are particularly suitable for use in gene therapy.

BACKGROUND OF THE INVENTION

Previous studies have shown that SV40 virions disrupted at pH 10.6 [Christensen, M. & Rachmeler, M. (1976) Virology 75:433–41] or by reducing disulfide bonds [Colomar, M. C., et al. (1993) J. Virol. 67:2779–2788] may be reassociated to form infectious SV40 aggregates. The early attempts to package in vitro foreign DNA in these aggregates [Christensen & Rachmeler (1976) ibid] produced infectious products which did not resemble SV40 virions. Furthermore, their resistance to DNase has not been tested. Later, in vitro packaging experiments [Colomar et al. (1993) ibid.] did not yield particles with infectivity above the level of naked DNA.

Recently, pseudocapsids of the closely related murine polyoma virus, prepared from polyoma VP1, were used as carriers for heterologous DNA into mammalian cells [Forstova, J., et al. (1995) Hum. Gene Therapy 6:297–306]. The pseudo-capsid protected 2–30% of the input DNA from DNase I digestion. When a plasmid carrying the cat gene was tested, most of the DNA which was protected from DNase I appeared as a ~2 kb fragment, while the input plasmid was significantly larger (exact size was not reported), suggesting that each DNA molecule was only partially protected against DNases. Infectious units were not measured in those experiments. The DNA transferred into recipient cells was functional in gene expression, albeit at a very low efficiency. With a 1.6 kb DNA fragment which carries the polyoma middle T-antigen, <30 transformed foci were obtained per 1 $\mu$g of input DNA. Similarly, a low level of CAT activity was observed with the plasmid carrying the cat gene.

SV40 is a simian papovirus, with a small double-stranded circular DNA genome of 5.2 kb [reviewed in Tooze, J. (1981) DNA Tumor Viruses. Cold Spring Harbor Laboratory, Cold Spring Harbor, N.Y.]. The viral capsid, surrounding the viral mini-chromosome, is composed of three viral-coded proteins, VP1, VP2, and VP3. Recent X-ray crystallographic studies on SV40 structure at 3.8 Å resolution [Liddington, R., et al. (1991) Nature 354:278–282] revealed that the outer shell of the virion particle is composed of 72 pentamers of VP1, 60 hexavalent and 12 pentavalent. The VP2 and VP3 appear to bridge between the VP1 outer shell and the chromatin core. The VP1 pentamers have identical conformations, except for the carboxy-terminal arms, which tie them together. Five arms extend from each pentamer and insert into the neighboring pentamers in three distinct kinds of interactions. It appears that this construction facilitates the use of identical building blocks in the formation of a structure that is sufficiently flexible as required for the variability in packing geometry [Liddington et al. (1991) ibid.].

Another protein encoded by the late regions of SV40 (which also encoded the three capsid proteins VP1, VP2 and VP3) is the agnoprotein, also called LP1. This is protein a small, 61 amino acid protein. Although the agnoprotein was not found in the viral capsid, it is thought to expedite viral assembly in vivo [Resnick, J & Shenk, T. (1986) J. Virol. 60:1098–1106; Ng, S. C., et al. (1985) J. Biol. Chem. 260:1127–1132; Carswell, S. & Alwine, J. C. (1986) J. Virol. 60:1055–1061].

The major hindrance in beginning to use the SV40 pseudovirions in preliminary experiments in humans is the present need for a viral helper for encapsidation. This results in pseudoviral stocks that contain also wild type SV40. Because of the similarity in properties (shape, size and density) between the pseudovirions and the helper, they cannot be separated by physical means. An ideal way to prepare pseudovirions for therapeutic purposes for human use would be by in vitro packaging. This would provide maximal safety, since all steps of the preparation can be well controlled. Ex vivo administration would circumvent problems associated with immune response.

Viral packaging in vivo occurs by gradual addition and organization of capsid proteins around the SV40 chromatin [Garber, E. A., et al. (1980) Virology 107: 389–401; Bina, M. (1986) Comments Mol. Cell Biophys. 4:55]. The three capsid proteins VP1, VP2 and VP3 bind to DNA non-specifically [Soussi, T. (1986) J. Virol. 59:740–742; Clever, J., et al. (1993) J. Biol. Chem. 268:20877–20883]. How the specific recognition between the viral capsid proteins and its DNA is achieved remains unclear. The packaging of SV40 using pseudovirions, in which most of the viral DNA is replaced by other sequences has been investigated [Oppenheim, A., et al. (1986) Proc. Natl. Acad. Sci. USA 83:6925–6929]. The pseudoviral particles are prepared by encapsidating plasmids that carry the SV40 origin of replication (ori) and the packaging signal (ses) [Oppenheim, A., et al. (1992) J. Virol. 66:5320–5328]. The model suggests that ses serves several functions in SV40 packaging: as a sensor for the level of the late viral proteins in the transition from replication and/or transcription to packaging, in nucleosomal reorganization and the initiation of viral assembly [Oppenheim, A., et al. (1994). J. Mol. Biol. 238:501–513] and probably also as a nucleation center for viral assembly [Dalyot-Herman, N. et al. (1996) J. Mol. Biol. 259:69–80].

The pseudovirions, carrying various genes of therapeutic interest, are very efficient in DNA transfer into a wide range of cells, including human bone marrow cells, and are therefore potential vectors for gene therapy [Oppenheim et al. (1986) ibid.; Oppenheim A., et al. (1987) Ann. New York Acad. Sci. 511:418–427; Dalyot, N. & Oppenheim, A. (1989) Efficient transfer of the complete human beta-globin gene into human and mouse hemopoietic cells via SV40 pseudovirions. In: Gene Transfer and Gene Therapy (Beaudet, A. L., Mulligan R, I. M. Verma, eds), pp. 47–56, Alan R. Liss, Inc., New York; Oppenheim, A., et al. (1992) Development of somatic gene therapy: A simian virus 40 pseudoviral vector for hemopoietic cells. In Genetic Among Jews (Bonne-Tamir, B., A. Adams, eds), pp. 365–373, Oxford University Press, Oxford]. The ideal way to prepare pseudovirions for therapeutic purposes for human use is by in vitro packaging. This would provide maximal safety, since all steps of the preparation can be well controlled.

SUMMARY OF THE INVENTION

The present invention relates to construct capable of infecting a mammalian cell comprising at least one semi-purified or pure SV40 capsid protein and a constituent selected from the group consisting of an exogenous DNA encoding an exogenous protein or peptide product, or encoding therapeutic RNA, or itself a therapeutic product, a vector comprising an exogenous DNA encoding an exogenous protein or peptide product, or encoding therapeutic RNA, or itself a therapeutic product, an exogenous RNA encoding an exogenous protein or peptide product or itself a therapeutic product, a vector comprising an exogenous RNA encoding an exogenous protein or peptide product or itself a therapeutic product, an exogenous protein or peptide product, and antisense RNA, ribozyme RNA or any RNA or DNA which inhibits or prevents the expression of undesired protein/s in said mammalian cell; and optionally further comprising operatively linked regulatory elements sufficient for the expression and/or replication of said exogenous protein in a mammalian cell.

The construct of the invention may optionally further comprise additional SV40 protein or proteins, preferably SV40 agnoprotein.

Constructs according to the invention may comprise as said constituent exogenous circular or linear DNA encoding an exogenous protein or peptide product, or is itself a therapeutic product, or a vector comprising exogenous DNA encoding a therapeutic RNA, or encoding an exogenous protein or peptide product.

The said protein product is preferably a therapeutic protein or peptide product which is not made or contained in mammalian cells, or is DNA which encodes a therapeutic protein or peptide product which is made or contained in such cells in abnormally low amount, or is DNA which encodes a therapeutic protein or peptide product which is made or contained in such cells in defective form or is DNA which encodes a therapeutic protein or peptide product which is made or contained in mammalian cells in physiologically abnormal or normal amount and can be an enzyme, a receptor, a structural protein, a regulatory protein or a hormone.

The constructs of the invention may comprise SV40-derived ori DNA sequence as said replication regulatory element and may further comprise DNA sequences encoding one or more regulatory elements sufficient for the expression of said exogenous RNA or exogenous protein or peptide in said mammalian cell.

In other embodiments, in constructs according to the invention said constituent is exogenous RNA, preferably RNA which encodes a therapeutic protein or peptide product which is not made or contained in said cell, or is RNA which encodes a therapeutic protein or peptide product which is made or contained in said cell in abnormally low amount, or is RNA which encodes a therapeutic protein or peptide product which is made contained in said cell in defective form, or is RNA which encodes a therapeutic protein or peptide product which is made or contained in said cell in physiologically abnormal or normal amount, said RNA having regulatory elements, including translation signal/s sufficient for the translation of said protein or peptide product in said mammalian cell, operatively linked thereto.

In other embodiments, the constructs according to the invention may comprise as said constituent an exogenous protein or peptide product, which can be a therapeutic protein or peptide product which is not made or contained in mammalian cells, or is a therapeutic protein or peptide product which is made or contained in such cells in abnormally low amount, or is a therapeutic protein or peptide product which is made or contained in such cells in defective form or is a therapeutic protein or peptide product which is made or contained in mammalian cells in physiologically abnormal or normal amount.

In further embodiments, the constructs according to the invention may comprise as said constituent antisense RNA or DNA or ribozyme RNA, or any RNA or DNA which inhibits or prevents the expression of undesired protein/s in mammalian cells.

The mammalian cells can be hemopoietic cells, such as bone marrow cells, peripheral blood cells and cord blood cells or liver cells, epithelial cells, endothelial cells, liver cells, epidermal cells, muscle cells, tumor cells, nerve cells and germ line cells.

The invention further relates to a method for the in vitro construction of SV40 viruses or pseudoviruses comprising exogenous nucleic acid comprising the steps of bringing a semi-purified or pure SV40 capsid protein or a mixture of at least two such proteins into contact with the exogenous nucleic acid to give recombinant SV40 viruses or with a vector comprising the exogenous nucleic acid to give pseudoviruses; and optionally subjecting the SV40 viruses or pseudo-viruses thus formed to digestion by nuclease to remove non-packaged DNA.

In the method of the invention, at least one other SV40 protein, preferably SV40 agnoprotein, can be added to the mixture of the SV40 capsid protein/s and the nucleic acid.

The DNA employed in the method of the invention can be DNA which encodes a therapeutic protein or peptide product which is not made or contained in mammalian cells, or is DNA which encodes a therapeutic protein or peptide product which is made or contained in such cells in abnormally low amount, or is DNA which encodes a therapeutic protein or peptide product which is made or contained in such cells in defective form or is DNA which encodes a therapeutic protein or peptide product which is made or contained in such cells in physiologically abnormal or normal amount or is DNA which encodes a therapeutic RNA.

The therapeutic protein or peptide product can be an enzyme, a receptor, a structural protein, a regulatory protein or a hormone.

The nucleic acid employed in the method of the invention can alternatively be exogenous RNA, wherein said RNA is RNA which encodes a therapeutic protein or peptide product which is not made or contained in mammalian cells, or is RNA which encodes a therapeutic protein or peptide product which is made or contained in such cells in abnormally low amount, or is RNA which encodes a therapeutic protein or peptide product which is made or contained in such cells in defective form or is RNA which encodes a therapeutic protein or peptide product which is made or contained in such cells in physiologically abnormal or normal amount and wherein said RNA has regulatory elements, including translation signal, sufficient for the translation of said protein product in mammalian cells, operatively linked thereto.

The method of the invention can also be used for the in vitro construction of recombinant SV40 viruses or pseudoviruses comprising an exogenous protein or peptide comprising the steps of bringing a semi-purified or purified SV40 capsid protein or a mixture of at least two such proteins into contact with the exogenous protein to give recombinant SV40 viruses or pseudoviruses; and optionally purifying the recombinant viruses or pseudoviruses thus obtained from any non-packaged protein.

In addition, the method of the invention can be used for the in vitro construction of SV40 pseudoviruses comprising exogenous antisense RNA, or ribozyme RNA or RNA or DNA which inhibits or prevents the expression of undesired protein/s in a mammalian cell, comprising the steps of bringing a semi-purified or pure SV40 capsid protein or a mixture of at least two such proteins into contact with the exogenous antisense RNA, or ribozyme RNA, or RNA or DNA which inhibits or prevents the expression of undesired protein/s in a mammalian cell, to give recombinant SV40 pseudoviruses; and optionally subjecting the SV40 pseudoviruses thus formed to digestion by nuclease to remove non-packaged DNA.

In a further aspect, the invention relates to mammalian cells infected with the constructs of the invention or with constructs obtained by any of the methods of the invention.

Still further, the invention relates to a method of providing a therapeutic DNA, RNA, protein or peptide product or antisense RNA to a patient in need of such product by administering to the patient a therapeutically effective amount of the SV40 viruses or pseudoviruses of the invention or a therapeutically effective amount of infected cells according to the invention.

Pharmaceutical compositions comprising as active ingredient a therapeutically effective amount of the SV40 viruses or pseudoviruses according to the invention or a therapeutically effective amount of infected cells according to the invention are also within scope of this application.

Nuclear extracts [Schreiber, E., et al, (1989) Nucl. Acids Res. 15:6419–6436] were prepared from Sf9 cells infected with the three recombinant baculoviruses expressing VP1, VP2 and VP3. Samples were adsorbed onto Formvar-carbon-coated copper grids and stained with 1% phosphotungstase, pH 7.2. The samples were viewed in a Philips CM-12 electron microscope, used at a voltage of 100 kV, and photographed at a magnification of ×60,000. The bar represents 50 nm.

Figure 1A:
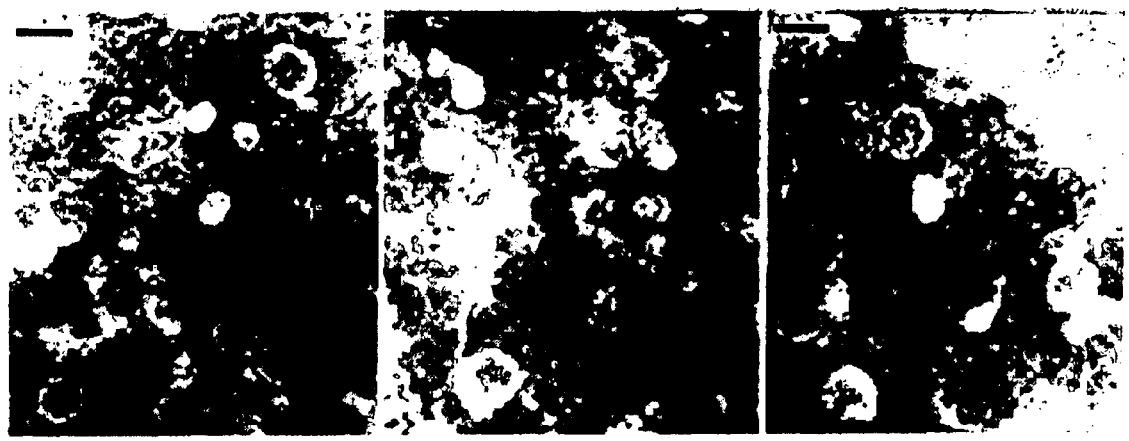
FIGS. 1(a) and 1(b): Self-Assembly of the SV40 capsid proteins

FIG. 1(a): Three fields of nuclear extracts of Sf9 cells infected with three recombinant baculoviruses, expressing VP1, VP2 and VP3.

Figure 1B:
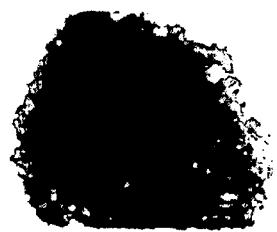

FIG. 1(b): Wild type SV40, shown for comparison.

Figure 2A:
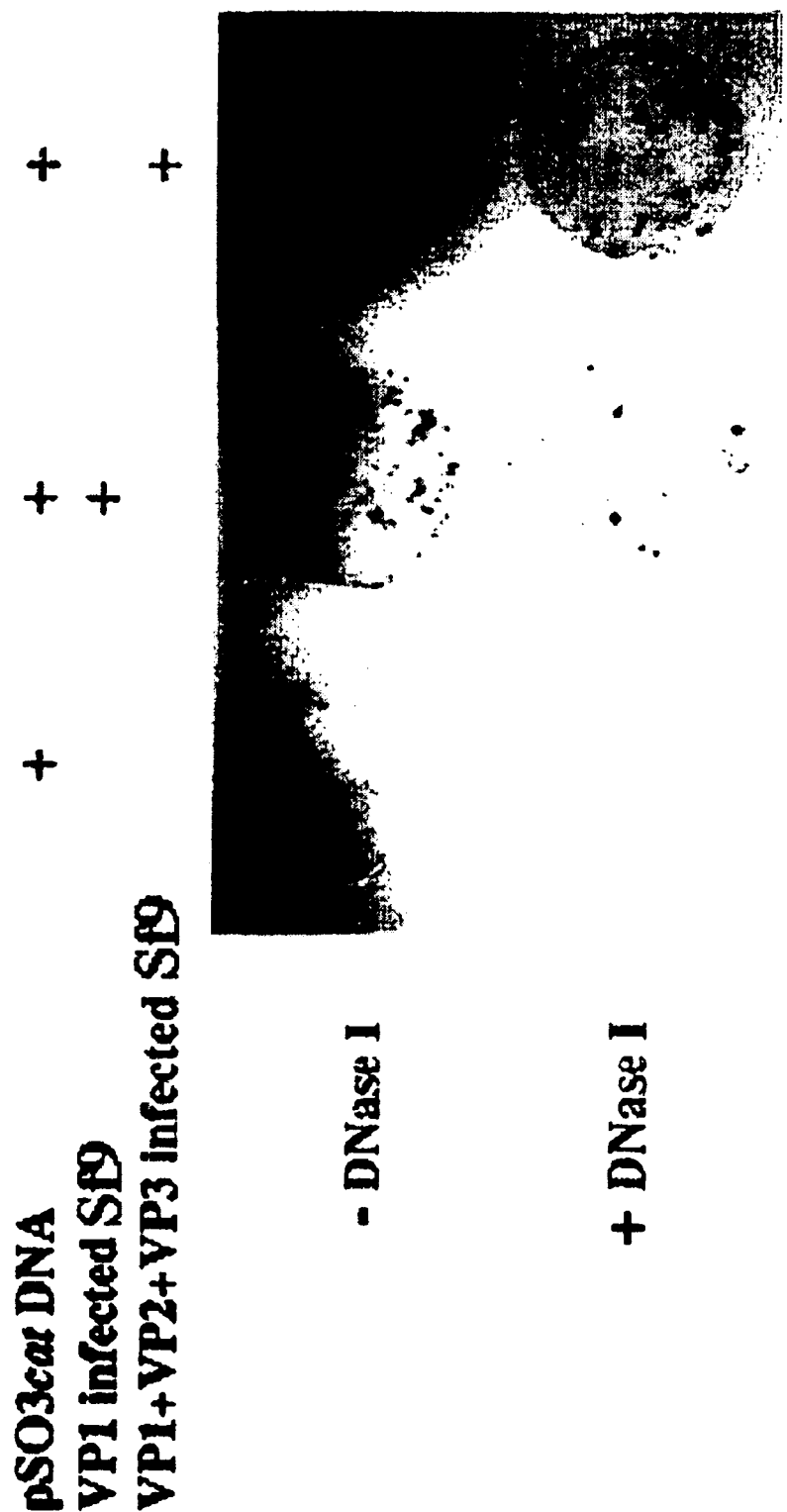
Figure 2B:
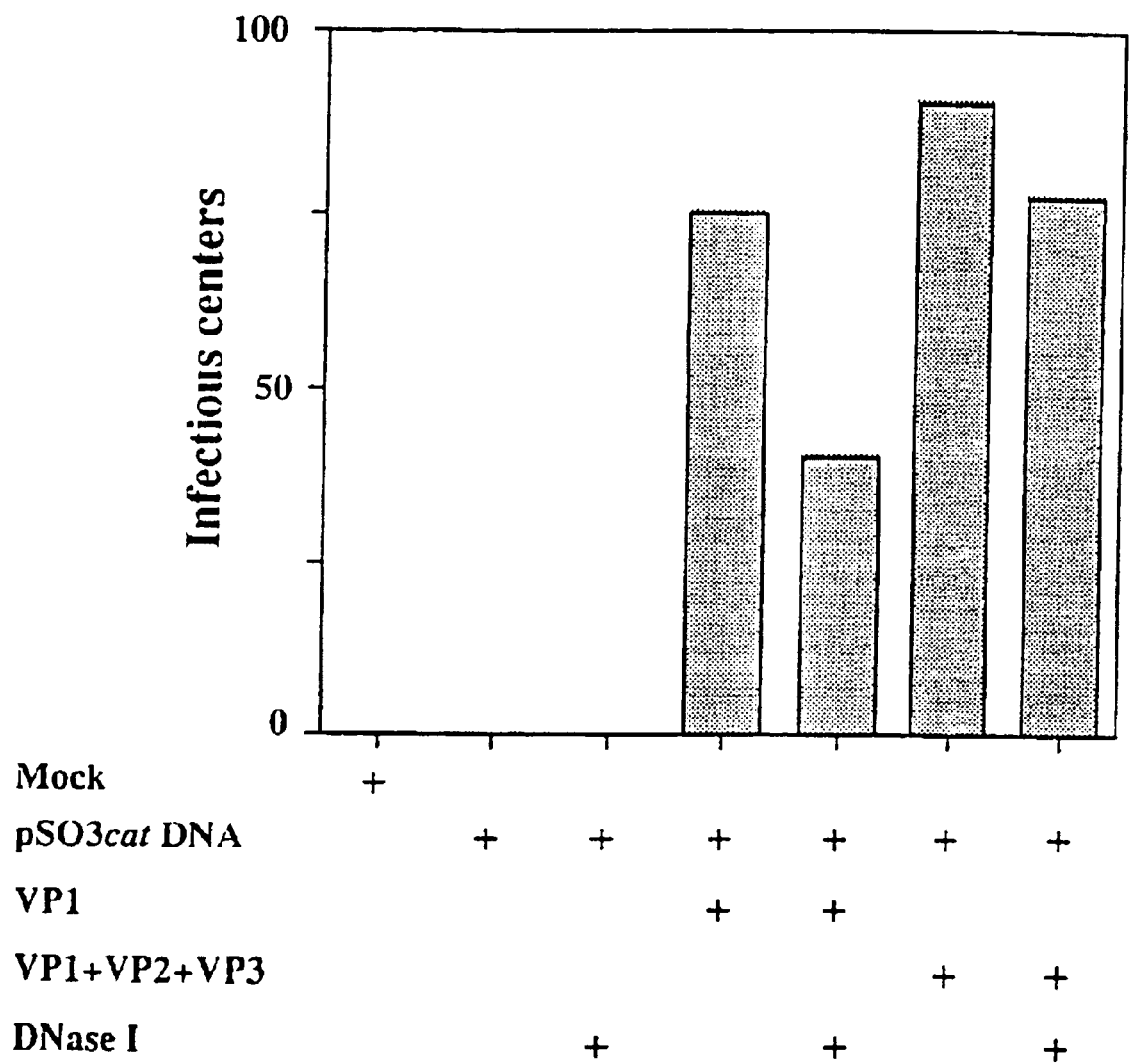
Figure 2C:
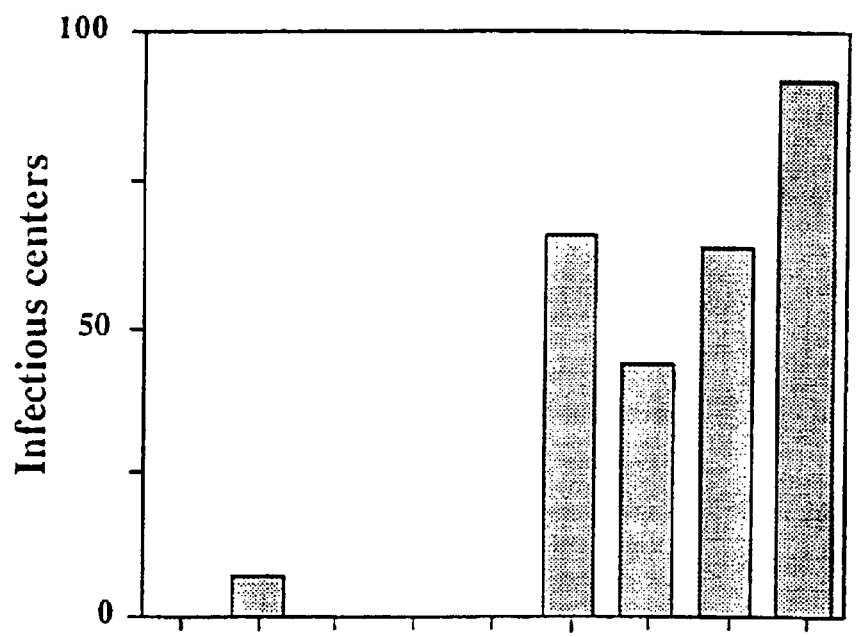

FIGS. 2(a)–2(c): Infectivity of SV40 virions and pSO3cat pseudo virions packaged in vitro.

Products of the in vitro packaging reaction were assayed for infectious units in situ hybridization, following infection of CMT4 monolayers.

FIG. 2(a): Autoradiograms showing infections centers produced by pSO3cat DNA packaged in vitro, using nuclear extracts of Sf9 cells infected either with recombinant baculovirus expressing VP1 or with the three recombinant viruses, as designated.

FIG. 2(b): Quantification of the results shown in FIG. 2(a).

FIG. 2(c): In vitro packaging of SV40 DNA, using nuclear extracts of Sf9 cells, uninfected or infected, as designated.

FIGS. 3(a)–3(d): Physical association of pSO3cat plasmid DNA with the capsid protein.

Figure 3A:
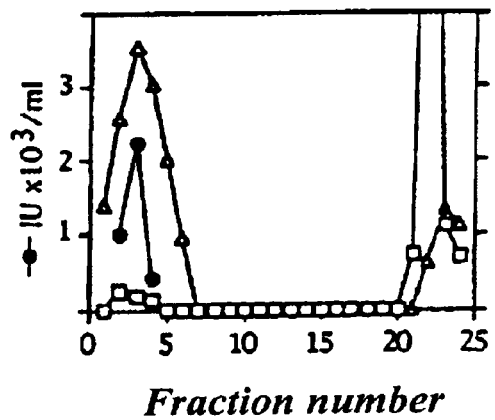

FIG. 3(a): The reaction products were placed on top of a 5–35% sucrose gradient in 10 mM TrisHCl pH 7.4/150 mM NaCl, with a 2M sucrose cushion, and centrifuged (SW 50.1 rotor) at 35000 rpm for 120 min., at 4° C. Fractions were collected from the bottom. Δ—SV40 capsid proteins, assayed by SDS-PAGE and western blotting with anti-VP1 antibody (Sandalon, Z., Herman-Dalyot, N., Oppenheim, A. B. And Oppenheim, A. Submitted for publication). □—DNA was analyzed following treatment with 0.4M NaOH in 25 mM EGTA and 20 mM DTT at 37° C. for 30 min., by electrophoresis on 1% agarose gels and Southern blotting, with pML2 as a probe. O-IU were assayed as described in FIG. 2.

Figure 3B:
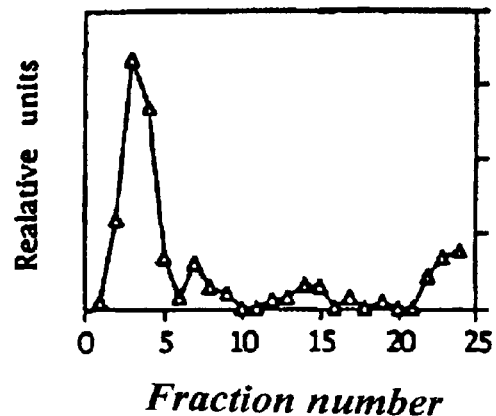

FIG. 3(b): Nuclear extracts of Sf9 cells infected with the three recombinant baculoviruses. The fractions were analyzed by SDS-PAGE as in (a).

Figure 3C:
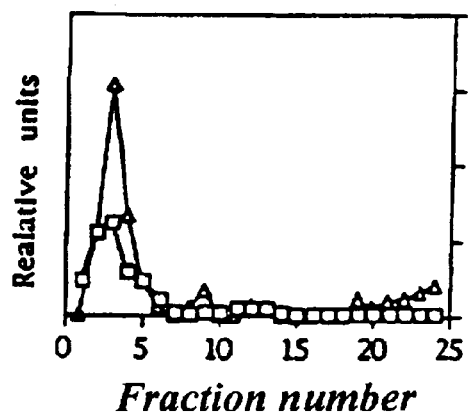

FIG. 3(c): SV40 virions, analyzed as described for (a). Δ—SV40 capsid proteins; □—SV40 DNA.

Figure 3D:
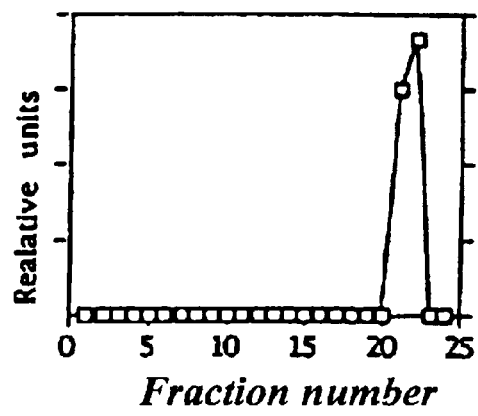

FIG. 3(d): pSO3cat DNA (1 μg). The fractions were analyzed by electrophoresis on 1% agarose gels and EtdBr staining.

Figure 4A:
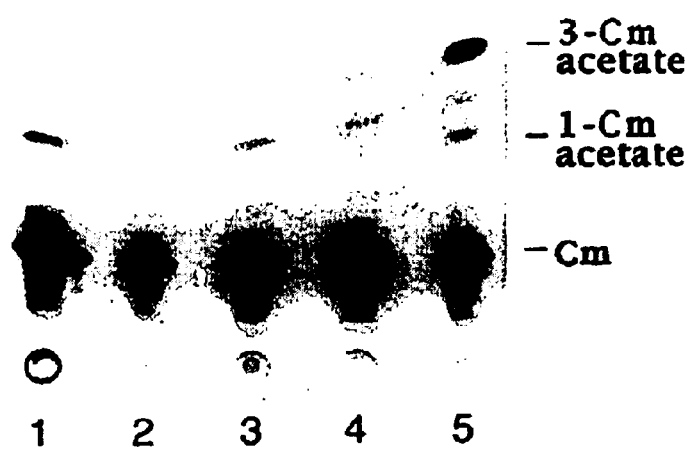
Figure 4B:
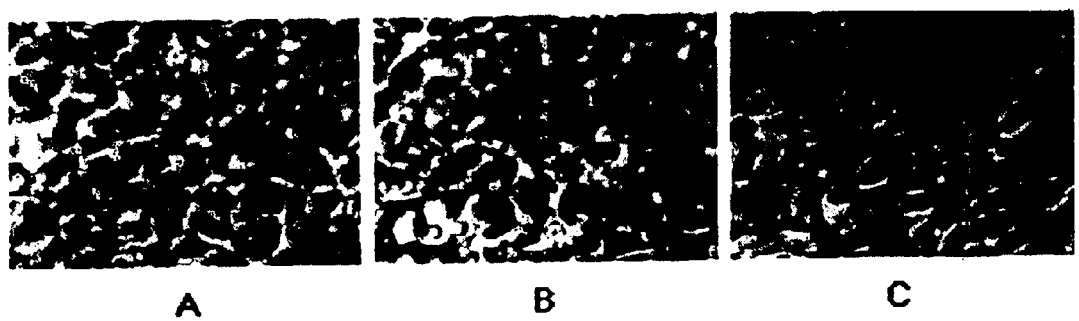

FIGS. 4(a) and 4(b): Expression of the transmitted DNA molecules.

FIG. 4(a): CMT4 cells, infected with in vitro packaged pSO3cat DNA, were assayed for CAT activity 3 days post infection. Essentially as previously described [Oppenheim. A., et al., (1986) Proc. Natl. Acad. U.S.A. 83:6925–6929], for 60 min. at 37°, using extracts of $10^6$ cells/assay.

1—No extract negative control;
2—Mock infected CMT4 control;
3—Control cells "infected" with pSO3cat DNA only;
4—Cells infected with in vitro packaged pSO3cat; moi of 1-IU per $2\times10^4$ cells;
5—Cells infected at a moi of 1-IU per $1\times10^4$ cells.

FIG. 4(b): Lysis of CV1 cells infected with in vitro packaged virions.

A—Mock infected;
B—"Infected" with DNA only;
C—Infected with in vitro packaged SV40.

DETAILED DESCRIPTION OF THE INVENTION

The present invention relates to constructs capable of infecting a mammalian cell, comprising at least one semi-purified or pure SV40 capsid protein and a constituent selected from the group consisting of an exogenous DNA encoding an exogenous protein or peptide product, or encoding a therapeutic RNA, or itself a therapeutic product, a vector comprising exogenous DNA encoding an exogenous protein or peptide product, or encoding a therapeutic RNA, or itself a therapeutic product, an exogenous RNA encoding an exogenous protein or peptide product or itself a therapeutic product, a vector comprising an exogenous RNA encoding an exogenous protein or peptide product, or itself a therapeutic product, an exogenous protein or peptide product, and antisense RNA, ribozyme RNA or any RNA or DNA which inhibits or prevents the expression of undesired protein/s in a mammalian cell, and optionally further comprising operatively linked regulatory elements sufficient for the expression and/or replication of said exogenous therapeutic RNA or of an exogenous protein or peptide in a mammalian cell.

The construct of the invention may optionally further comprise additional SV40 protein or proteins, preferably SV40 agnoprotein.

In specific embodiments, the constructs of the invention comprise a mixture of at least two semi-purified or pure SV40 capsid proteins.

In a further specific embodiment, the constructs of the invention comprise a mixture of three semi-purified or pure SV40 capsid proteins.

The SV40 capsid proteins of the invention can be semi-purified or pure VP1 or VP2 or VP3.

The constructs of the invention may comprise as said constituent an exogenous circular or linear DNA encoding an exogenous protein or peptide product, or itself a therapeutic product, or encoding therapeutic RNA, or a vector comprising exogenous DNA encoding therapeutic RNA or encoding an exogenous protein or peptide product. Delivery into cells of linear DNA, by infecting the cells with constructs of the invention comprising such linear DNA, may be advantageous for recombination, i.e. integration into the cellular genome for stable expression.

Specifically, said DNA is DNA which encodes a therapeutic protein product or is itself a therapeutic product which is not made or contained in said cell, or is DNA which encodes a therapeutic protein or peptide product which is made or contained in said cell in abnormally low amount, or is DNA which encodes a therapeutic protein or peptide product which is made or contained in said cell in defective form or is DNA which encodes a therapeutic protein or peptide which is made or contained in said cell in physiologically abnormal or normal amount or encodes a therapeutic RNA.

The therapeutic protein or peptide product can be any protein of interest, such as an enzyme, a receptor, a structural protein, a regulatory protein or a hormone. Of particular interest are proteins which are missing or defective in patients suffering genetic disorders. A specific example may be β-globin, missing in patients with β-thalassemia.

The constructs of the invention may optionally comprise SV40-derived ori DNA sequence as said replication regulatory element. The exogenous DNA may optionally have, operatively linked thereto, additional DNA sequence/s encoding one or more regulatory elements sufficient for the expression of the exogenous protein or peptide encoded thereby in mammalian cells.

In an additional aspect, in constructs of the invention said constituent is exogenous RNA, particularly RNA which encodes a therapeutic protein or peptide product which is not made or contained in said cell, or is RNA which encodes a therapeutic protein or peptide product which is made or contained in said cell in abnormally low amount, or is RNA which encodes a therapeutic protein or peptide product which is made or contained in said cell in defective form, or is RNA which encodes a therapeutic protein or peptide product which is made or contained in said cell in physiologically abnormal or normal amount, said RNA having regulatory elements, including translation signal/s sufficient for the translation of said protein or peptide product in said mammalian cell, operatively linked thereto.

As in the embodiments containing RNA, the therapeutic protein or peptide product encoded by the exogenous RNA may be any protein of interest, such as an enzyme, a receptor, a structural protein, a regulatory protein or a hormone.

Packaging of RNA may be advantageous for "short term", transient gene activity. Packaging of RNA in SV40 pseudovirions, instead of, or in addition to DNA, will allow delivery of mRNA into mammalian cells. The mRNA should include mammalian translation signal, for example Kozak sequences. Such constructs will facilitate transient production of proteins, having high specific function, in vivo.

The constructs of the invention will also enable the delivery of ribozyme RNA, which can be used in any application where specific RNA cleavage is desired, as an anti-AIDS agent or as an agent against other viral infections or for other therapeutic purposes.

A specific example may be chronic myelogenous leukemia (CML). CML is a clonal stem-cell disorder which accounts for about 25 percent of all leukemias, with an annual incidence of one per 100,000 population, affecting all age groups, with a peak incidence in the fifth and sixth decades of life. Clinically, CML is characterized by a triphasic course. The initial chronic phase, often develops insidiously and is marked by an increased pool of committed myeloid progenitor cells. After a few weeks to several years (median duration 42 months) the disease turns into a phase of "acceleration", which later progresses to the acute phase. The median survival, from diagnosis, in the acute phase is approximately 4 months.

CML is genetically characterized by the presence of the Philadelphia chromosome (Ph'), which is the result of reciprocal translocation between chromosomes 9 and 22. At the molecular level, the proto-oncogene abl from chromosome 9 is translocated to the breakpoint cluster region (bcr) on chromosome 22, creating two major types of junctions: L-6 and K-28, each resulting in the formation of bcr/abl hybrid gene, expressing a fusion protein of 210 kd, which causes the disease. Possible use of antisense (18-mer) oligonucleotides, or DNA encoding antisense RNA, directed against the expression of the bcr/abl gene as tumor specific agents which alter the transformed phenotype of leukemia cells cultured in vitro has already been demonstrated [Szczylik, C. et al. (1991). Science, 253:562–565; Garcia-Hernandaz, B. & Sanchez-Garcia, I. (1996) Mol. Medicine, 2:1076–1551].

Therefore, the constructs according to the invention may comprise as said constituent antisense RNA or DNA encoding antisense or ribozyme RNA, or any RNA or DNA which inhibits or prevents the expression of undesired protein/s or peptide/s in mammalian cells.

In this specific embodiment, said antisense RNA or DNA encoding antisense RNA can be directed against the expression of the bcr/abl transcript, or against an HIV transcript.

In additional embodiments, the constructs of the invention may comprise as said constituent an exogenous protein or peptide product.

In preferred such constructs, said constituent is exogenous protein or peptide product is, respectively, a therapeutic protein or peptide product which is not made or contained in said cell, or is a therapeutic protein or peptide product which is made or contained in said cell in abnormally low amount, or is a therapeutic protein or peptide product which is made or contained in said cell in defective form or is a therapeutic protein or peptide product which is made or contained in said cell in physiologically abnormal or normal amount.

The delivery of packaged proteins or peptides will also facilitate their transient function in vivo. This approach will be used when long term effects of the packaged protein are not required or may be dangerous. Thus, for example, the delivery of packaged proteins may be useful in cases where transient local production of appropriate growth factors, for example, FGF (Fibroblast Growth Factor) is required, to accelerate internal wound healing or post-operative incision healing. Local transient introduction of blood clotting factors may be desirable for prevention of hemorrhage and introduction of anti-coagulating factors may be desirable for dissolving unwanted blood clots. Application of infecting pseudo-virions on site may be by catheters or any other suitable physical means.

Some proteins may have specific function on the fate of DNA delivery. The constructs of the invention will enable the delivery of mRNA encoding for a protein which promotes homologous recombination, or the delivery of such protein itself. Pseudovirions carrying a gene will be used in co-infection, together with constructs comprising as said constituent mRNA coding for proteins which promote homologous recombination such as REC A, or construct comprising as a constituent such protein/s. This technique will enable gene replacement therapy.

The constructs of the invention are capable of infecting mammalian, particularly human cells. Specific cells may be hemopoietic cells, such bone marrow cells, peripheral blood cells and cord blood cells, or liver cells, epithelial cells, endothelial cells, liver cells, epidermal cells, muscle cells, tumor cells, nerve cells and germ line cells.

In another aspect, the invention relates to a method for the in vitro construction of SV40 viruses or pseudoviruses comprising exogenous nucleic acid, comprising the steps of bringing a semi-purified or pure SV40 capsid protein or a mixture of at least two such proteins into contact with said exogenous nucleic acid to give recombinant SV40 viruses or with a vector comprising said exogenous nucleic acid to give pseudoviruses; and optionally subjecting the SV40 viruses or pseudoviruses thus formed to digestion by nuclease to remove non-packaged DNA.

The SV40 capsid protein are preferably semi-purified or pure SV40 VP1, VP2 or VP3.

The method of the invention may employ, in addition to said semi-purified or pure SV40 capsid protein/s and said nucleic acid, at least one other SV40 protein, preferably SV40 agnoprotein.

The exogenous nucleic acid is preferably circular or linear DNA or is RNA. The exogenous nucleic acid preferably encodes a therapeutic protein or peptide product or is itself therapeutic product.

In specific embodiments, said DNA or RNA are DNA or RNA which encode a therapeutic protein or peptide product which is not made or contained in said cell, or which encode a therapeutic protein or peptide product which is made or contained in said cell in abnormally low amount, or which encode a therapeutic protein or peptide product which is made or contained in said cell in defective form or which encode a therapeutic protein or peptide product which is made or contained in said cell in physiologically abnormal or normal amount or is a DNA which encodes a therapeutic RNA.

Said exogenous DNA or RNA preferably encode a therapeutic protein or peptide product which is an enzyme, a receptor, a structural protein, a regulatory protein or a hormone.

In the method of the invention, SV40-derived ori DNA sequence may be added and said exogenous nucleic acid optionally has DNA sequence encoding one or more regulatory elements, sufficient for the expression of said exogenous protein or peptide in said mammalian cell, operatively linked thereto.

When said nucleic acid is exogenous RNA, it has to have the necessary regulatory signals, including a translation signal, sufficient for the translation of said protein or peptide product in a mammalian cell, operatively linked thereto.

In a further embodiment, the invention relates to a method for the in vitro construction of recombinant SV40 viruses or pseudoviruses comprising as said constituent an exogenous protein or peptide comprising the steps of bringing a semi-purified or pure SV40 capsid protein or a mixture of at least two such proteins into contact with an exogenous protein or peptide, to give recombinant SV40 viruses or pseudoviruses, and optionally purifying the recombinant viruses or pseudoviruses thus obtained from any non-packaged protein.

In this embodiment, the exogenous protein or peptide can be, respectively, a naturally occurring or recombinant protein or peptide, a chemically modified protein or peptide, or a synthetic protein or peptide.

The exogenous protein or peptide product are, respectively, a therapeutic protein or peptide product not made or contained in a mammalian cell, or are a therapeutic protein or peptide product made or contained in said cell in abnormally low amount or are a therapeutic protein or peptide product made or contained in said cell in defective form or are a therapeutic protein or peptide product made or contained in said cell in physiologically abnormal or normal amount.

In addition, the method of the invention can be used for the in vitro construction of SV40 pseudoviruses comprising antisense RNA, or exogenous DNA encoding antisense RNA, or ribozyme RNA, or RNA or DNA which inhibits or prevents the expression of undesired protein/s or peptide/s in a mammalian cell, comprising the steps of bringing a semi-purified or pure SV40 capsid protein or a mixture of al least two such proteins into contact with the exogenous antisense RNA or exogenous DNA encoding antisense RNA, or ribozyme RNA, or RNA or DNA which inhibits or prevents the expression of undesired protein/s or peptide/s in a mammalian cell, to give recombinant SV40 pseudoviruses; and optionally subjecting the SV40 pseudoviruses thus formed to digestion by nuclease to remove non-packaged DNA.

In this embodiment, the said antisense RNA or DNA encoding antisense RNA can be directed against the expression of bcr/abl transcripts, or against an HIV transcripts.

The method of the invention is suitable for the preparation of constructs which are capable of infecting any suitable mammalian cell. Specific cells are hemopoietic cells, such as bone marrow cell, peripheral blood cells and cord blood cells, or liver cells, epithelial cells, endothelial cells, liver cells, epidermal cells, muscle cells, tumor cells, nerve cells and germ line cells.

In yet a further aspect, the invention relates to a mammalian, preferably human cell infected with any of the constructs of the invention, or constructs obtained by any of the methods of the invention.

Still further, the invention concerns a method of providing a therapeutic DNA, RNA, protein or peptide product or antisense RNA or DNA encoding antisense to a patient in need of such product by administering to said patient a therapeutically effective amount of any of the said SV40 viruses or pseudoviruses or a therapeutically effective amount of said infected cells.

The invention also relates to pharmaceutical compositions comprising as active ingredient a therapeutically effective amount of the SV40 virus or pseudoviruses of the invention or a therapeutically effective amount of the infected cells of the invention.

The constructs of the invention are very efficient in gene transfer into a variety of cells, including human hemopoietic cells and probably also stem cells. Thus, they may be suitable for treating a wide spectrum of diseases. Plasmids carrying the desired gene and the SV40 ori and, optionally ses, are encapsidated in COS cells, optionally with helpers, as SV40 pseudovirions, and transmitted into the target cells by viral infection. The prokaryotic DNA is removed after propagation in bacteria and before encapsidation. The constructs include only 200 bp of SV40 DNA, with cloning capacity of over 5 kb. Thus plasmids carrying over 95% human DNA are efficiently transferred into human hemopoietic cells.

The invention provides for safer and cheaper products for medical use, which may be prepared under aseptic conditions. A major advantage is that proteins are readily made in insect cells. While semi-purified proteins (nuclear extracts) are exemplified, purified proteins can be employed. Further, DNA is prepared in bacteria and can be purified before it is packaged. This ensures high purity and high quality DNA minimizing the chance for picking spontaneous mutations and/or rearrangements. In addition, in vivo pseudovirions are present in a solution which also contains constituents of the cells in which they were grown. In contrast, infection by retroviral vectors prepared in vivo is done by co-culturing of the patients cells with the producer cell-lines (usually murine). Although in vivo prepared viral sectors (such as adenoviruses or adeno-associated virus) can be purified, this may substantially increase production cost, as purification is also associated with loss of virion particles. In addition, in helper-free packaging cell-lines (of any virus) there is always a risk of contamination by recombinants. These could be either the wild-type virus or unknown recombination products, carrying potentially harmful (cellular) genes. The risk is completely abolished when packaging is done in vitro. Moreover, in vitro packaging can accommodate larger plasmids than in vivo packaged SV40 pseudovirions: The in vivo packaged pseudovirions accommodate only up to about 5.4 kb of DNA [Oppenheim, A. & Peleg, A. (1989) Gene 77:79–86]. In the present in vitro method about 7.5 kb have been packaged successfully, and larger plasmids can be packaged. Regulatory elements (e.g. β-globin, LCR), which interfere with packaging in vivo, are not expected to interfere with packaging in vitro. An additional important advantage is that the ses element is not required for in vitro packaging (Tables 2 and 3), reducing the size of the required SV40 sequences to about 100 bp, comprising the ori, in the exemplified experiments. Embodiments without even this element are also contemplated. In the present examples, the ori element was required for the assay of infectious units. The high flexibility afforded by the method and constructs of the invention may allow the development of gene targeting (or gene replacement therapy).

EXAMPLES

Cloning the Genes of the SV40 Capsid Proteins for Expression in Bacteria

First, plasmids designed to express the complete VP1, VP2 and VP3 polypeptides as fusion proteins to glutathion-S-transferase (GST) in E. coli [Smith, D. B. & Johnson, K. S. (1988) Gene 67:31–40]. The respective SV40 fragments were cloned into the vector with the aid of PCR. Expression level was high, leading to the production of insoluble inclusion bodies. Similarly, it was recently reported [Clever et al, ibid.] that a truncated VP2 fused to GST also yielded an insoluble product.

Preparation of Antibodies

The three GST-fusion capsid proteins were used to raise polyclonal antibodies in rabbits. Antibodies against GST-VP1 did not cross-react with VP2 and VP3. As expected, antibodies against GST-VP2 reacted both with VP2 and VP3, and did not cross-react with VP1.

Cloning the SV40 Late Genes for Expression in Insect Cells

SV40 DNA fragments were cloned into the plasmnid vectors pVL1393 and pVL1392 (commercially available from PharMingen, San Diego, Calif.), derived from Autographa californica nuclear polyhedrosis virus (AcMNPV) [Luckow, V. A. & Summers, M. D. (1988) 6:47–55; Luckow, V. A. & Summers, M. D. (1989) Virology 170:31–39] In these vectors expression of the foreign gene is driven by the strong promoter for the viral occlusion protein, polyhedrin. The genes for the capsid proteins were cloned into pVL1393 as follows: VP1 was cloned by introducing a StuI-BclI DNA fragment (SV40 coordinates 1463–2770) into the plasmid cleaved by restriction endonucleases SmaI and BglII. The VP2 gene was cloned by ligating a HincII-EcoRI fragment (522–1782) between the SmaI and EcoRI sites. The VP3 gene, which is nested in the VP2 gene (it is translated from an internal AUG signal), was cloned by using a Sau3AI-EcoRI fragment (874–1782) and the BamHI and EcoRI sites of pVL1393. A fourth late polypeptide, the agnoprotein (or LP1), encoded by the leader region of the late 16S mRNA, appears to play a role in expediting virion assembly [Carswell, S. & Alwine, J. C (1986) J. Virol. 60:1055–1061; Resnick, J. & Shenk, T. (1986) J. Virol. 60:1098–1106] The agnogene, a PvuII-MboI fragment (273–873), was cloned between the SmaI and BamHI sites of plasmid pVL1392.

The structures of the four recombinant plasmids were confirmed by restriction analysis and after propagation in E. coli. Sequence analysis was performed for the recombinant plasmids carrying VP2 and VP3. Recombinant baculovirus carrying the four respective genes were produced using the Baculogold™ kit (Baculovirus Expression Vector System, including linearized baculovirus DNA; kindly provided by PharMingen, California). The technique relies on homologous recombination between the plasmid and a modified type of baculovirus with a lethal deletion. Each of the recombinant plasmids was co-transfected, together with linearized DNA of the defective baculovirus, into Spodoptera frugiperda (Sf9) cells. Virus was harvested 4 days later, according to the protocol supplied by the manufacturer. To obtain high titer stocks each of the recombinant virus was amplified by 3 cycles of infection (5 cycles for the VP2 recombinant virus) of freshly seeded Sf9 cells [Summers, M. D. & Smith, G. E. (1988) A manual of methods for baculovirus vectors and insect cell culture procedures. Texas Agricultural Experiment Station, College Station, Tex.) The final titers of the 4 recombinant baculoviruses stocks were $2-4 \times 10^8$ pfu/ml.

The SV40 proteins were produced in Sf9 cells, infected at a multiplicity of 10 pfu/cell and grown at 27° C. Cells were harvested and the soluble proteins were analyzed by SDS-PAGE [Laemmli, E. K. (1970) Nature 277:80–685] and Western blotting [Harlow, E. & Lane, D. (1988) Antibodies, a laboratory manual. Cold Spring Harbor Laboratory, N.Y., Cold Spring Harbor] using antibodies raised against the corresponding GST-fusion proteins. Kinetic studies showed increasing levels of the SV40 proteins from 3 to 6 days postinfection.

The Three Capsid Proteins Assemble Spontaneously to Form SV40-like Particles

The SV40 capsid proteins were produced, separately, in Spodoptera frugiperda (SF9) cells from recombinant baculovirus each carrying the genes coding for VP1, VP2 or VP3. The cells were harvested and nuclear and cytoplasmic fractions were analyzed by SDS-PAGE and western blotting. The results demonstrated that VP1 and VP3 were preferentially present in the nuclear fraction, whereas VP2 was preferentially cytoplasmic (not shown). When the three proteins were co-expressed in the same cells (following infection with the three recombinant baculoviruses together), all three proteins were present in the nuclear fraction. The capsid proteins self-assembled to form SV40-like structures of various sizes. Electron microscopy of nuclear extracts of the infected cells showed abundance of "empty" SV40-like capsids and heterogeneous aggregates of variable size, mostly 20–45 nm (FIG. 1(a)). Under the same staining conditions wild type SV40 virions are 45 nm with well defined boundaries (FIG. 1(b)). Occasionally smaller, presumable empty or defective particles, are also seen in wild type SV40 stocks.

To purify VP1, nuclear extracts of infected cells were placed on 15–35% glycerol gradient with a 2M sucrose cushion. Western blot analysis and EM studies demonstrated that the majority of VP1 was present as high MW structures in 2 peaks, one at the cushion and the other at the bottom of the tube. About a third of the protein was present as pentamers (10S units; MW~210 kd). In most of the experiments, monomers were not seen. The results indicate that VP1 molecules readily form pentamers and high MW structures at this high concentration. VP1 pentamers and higher MW structures are stabilized by S-S bonds [Gharakhanian, E. et al. (1995) Virology 207:251–254] and by $Ca^{++}$ [Liddington et al., ibid.]. It appears that only at very low concentrations VP1 molecules may remain monomeric (Gharakhanian et al., ibid.].

Similar experiments, performed with nuclear extracts of cells containing the 3 capsid proteins, demonstrated that the three proteins co-precipitated together in the glycerol gradients in two high MW fractions, at the very bottom of the tube (fraction I) and at the cushion (fraction II). In addition, peaks corresponding to VP1 pentamers and to VP2 monomers were also seen.

In SV40, the three capsid proteins are expressed from a single promoter with complex regulatory controls, including several transcription start sites, alternative splicing to two major species, 16S RNA, producing the agnoprotein (which is not part of the capsid) and VP1 and 19S, producing VP2 and VP3. The two bicistronic messages contain internal translation initiation signals. This organization is thought to facilitate coordinated expression at the correct ratio for packaging (Sedman, S. A., et al. (1989) *J. Virol.* 63:3884–3893; Sedman, S. A. et al. (1990) *J. Virol.* 64:453–457]. Co-production of the capsid proteins VP1, VP2 and VP3 in Sf9 cells was performed by infecting with the 3 baculovirus species at equal multiplicities. Nevertheless, the ratio of the 3 proteins in fraction II was similar to the ratio obtained in monkey CMT4 cells [Gerard, R. D. & Gluzman, Y. (1985) *Mol. Cell. Biol.* 5:3231–3240] infected with wild type SV40. This was not true for fraction I. Furthermore, EM studies revealed that fraction II was relatively homogeneous, containing particles of approximately SV40 size, which appeared "empty", as they allow penetration of the stain. On the other hand the particles in fraction I were highly heterogeneous in size.

DNA is Packaged in the SV40 Capsids in vitro, Forming Infectious Particles

A. Packaging experiments were performed with SV40 DNA and with heterologous plasmid DNA. Nuclear extracts of Sf9 cells were prepared according to Schreiber [Schreiber, (1989) ibid]. 2 μl of nuclear extracts (protein concentration 1–2 μg/μl) were mixed by vortex with 1 μg DNA in a total volume of 4 μl and placed at 37° C. for 6 hr. Preliminary experiments showed that shorter incubation periods (1–4 hr) gave lower yields of infectious particles. $CaCl_2$ and $MgCl_2$ were added to final concentrations of 100 μM and 8 mM respectively, to a total volume of 6 μl, and the reactions were incubated for an additional 1 hr on ice. DNase I digestion was performed using 0.5 unit of enzyme for 10 min on ice, and stopped by the addition of EDTA to a final concentration of 5 mM.

The DNase I treatment was used to remove DNA which was not stably packaged. The reaction products were assayed for infectious units (IU) on CMT4 monolayers, grown in Dulbecco's modified Eagle's medium with 10% FBS, using a standard SV40 infection protocol. CMT4 are permissive African green monkey kidney cells that harbor the gene for SV40 T-antigen expressed from the inducible metallothionein promoter [Gerard, R. D. & Gluzman, Y. (1985) Mol. Cell. Biol. 5:3231–3240]. Sub-confluent monolayers were incubated with the packaging mixture for 120 min at 37° C., with occasional agitation, followed by the addition of fresh medium containing 0.1 mM $ZnCl_2$ and 1 μM $CdSO_4$ for the induction of T-antigen expression. Infective centers were scored by in situ hybridization. The number of infective centers obtained for a 6 μl reaction mixture was used in computing the titer of IU/ml (FIG. 2(a)).

The procedure yielded infectious units both with SV40 DNA (FIG. 2(c)) and with pSO3cat DNA (FIGS. 2(a) and 2(b)). A typical experiment, demonstrating infectivity of in vitro packaged pSO3cat, is shown in FIG. 2(a). Under these conditions naked DNA sometimes also entered the cells. However, the DNase I treatment completely removed the naked DNA background from the assay. The experiments showed that using the nuclear extracts containing VP1+VP2+VP3 directly, without purification on glycerol gradients, yielded 90 infectious centers, per 6 μl packaging reaction, equivalent to $1.5 \times 10^4$ infective units IU per ml. Pre-treatment before the infection with DNase I reduced the number to 77 ($1.2 \times 10^4$ IU/ml). Incubation with nuclear extracts containing VP1 alone produced 75 infectious centers ($1.2 \times 10^4$ IU/ml), almost the same as with the three capsid proteins. However, The pre-treatment with DNase reduced the number almost 2 fold, to 40 (a titer of $6.6 \times 10^3$ IU/ml). This was seen both for pSO3cat DNA (FIG. 2(b)) and for SV40 DNA (FIG. 2(c)), suggesting that the DNA in those particles was not as effectively protected from DNase I, under the conditions described below. These results suggest that VP2 and VP3 contribute to the stability of the DNA-capsid complexes. In the absence of DNase I treatment naked DNA was also sometimes infectious. However, DNase I digestion completely removed the naked background from the assay. Therefore, all subsequent experiments included DNase I digestion. FIG. 2(c) also demonstrates that presence of the SV40 capsid proteins is required for the production of infectious particles, as "packaging" with nuclear extracts of uninfected Sf9 gave negative results. Few "infectious units" were seen in cells treated with SV40 DNA only, demonstrating the ability of naked DNA to penetrate cells. DNase I treatment completely removed this background.

Insect cells were infected with three recombinant baculoviruses encoding for the three capsid proteins, VP1, VP2 and VP3, at moi 10 each. After 4 days nuclear extracts were prepared essentially as described by Schreiber [Schreiber, E., et al. (1989) *Nucleic Acids Res.* 15:6419–6436] by shaking the nuclei, isolated with 10% NP-40, in a buffer containing 20 mM HEPES pH 7.9, 0.4M NaCl, 1 mM EDTA, PMSF and leupeptin were added just before use. The nuclei from each 75×$cm^2$ culture bottle were extracted with 150 μl buffer.

The nuclear extract was used in packaging experiments performed exactly as described above. For each packaging reaction 2 µl nuclear extracts were mixed with 1 µg DNA (either SV40 or pSO3cat) in a total volume of 4 µl, for several hours at 37° C. The reaction mixture was transferred to ice, 2 µl of 0.4 mM CaCl$_2$ were added and incubated for 60 min on ice. This was followed by the addition of 2 µl containing 0.5 unit of DNase I, and the incubation continued for 10 min. on ice. The reaction was stopped by the addition of 2 µl of 25 mM EDTA (final concentration 5 mM). Serum-free medium was added (300 µl) and the mixture was applied to a sub-confluent CMT4 culture in a 6 cm diameter culture plate. The cultures were incubated at 37° C. with gentle agitation every 20 min. Two hours later the infection mixture was sucked off and 5 ml fresh medium containing 5% FBS was added. After about 40 hr, to allow replication of the DNA transmitted by the infectious particles, the monolayers were transferred to nitrocellulose layers and processed for hybridization.

B. In another study, the inventors investigated the properties of the self-assembled empty capsids shown in FIG. 1 and FIG. 3(b). It was found that DTT and EGTA induced dissociation of the self-assembled empty capsids. Therefore, an alternative protocol was devised, in which the proteins are pre-treated with DTT and EGTA prior to their incubation with the DNA. The DTT and EGTA are dialyzed out and replaced by Ca$^{++}$ ions. Nuclear extracts of Sf9 were prepared as described above [Shreiber et al. (1989), ibid.] from cells infected with the three recombinant baculoviruses expressing VP1, VP2 and VP3 at multiplicity of infection (moi) 10 for each recombinant baculovirus. For each packaging reaction, 10 µl of nuclear extracts, containing 10–15 µg protein, are incubated with DTT at a final concentration of 10 mM for 5 min at 33° C., with gentle shaking, to allow the capsid proteins to dissociate. The reactions are than cooled on ice, 1 µg of DNA is added to each reaction and the ingredients are thoroughly mixed by vortexing and incubated on ice for 30 min. Total volume for each reaction is 20 µl. The reaction mixtures are then dialyzed against a buffer containing 10 mM CaCl$_2$, 150 mM NaCl, 10 mM Tris-HCl pH 7.2 for 24 hr in the cold, with two changes.

This protocol yielded, in 4 different experiments, a titer of $1-2.5 \times 10^4$ IU/ml, which is similar to the titer obtained in the above described protocol A.

Physical Association between Capsids and DNA

To obtain physical evidence for the association of DNA with capsid particles, the reaction products were sedimented in a sucrose gradient. To prevent the action of endonucleases present in the nuclear extract, EDTA was added to a final concentration of 4 mM. Under these conditions, non-packed DNA, which sedimented at the top of the gradient (as does free plasmid DNA, FIG. 3(d)), remained intact and supercoiled, as was evident from agarose gel electrophoresis. The majority of the capsid proteins to the sucrose cushion, similarly to authentic SV40 (FIGS. 3(a) and 3(c)). A small portion of the DNA (pSO3cat) co-sedimented with the capsid proteins to the sucrose cushion. That DNA was visible on agarose gel electrophoresis and Southern blotting only after the particles were dissociated by treatment with EGTA and DTT at alkaline pH, suggests that it had been contained within particles. The DNA in those fractions migrated on the gel as did supercoiled pSO3cat DNA (not shown), indicating the presence of intact plasmid molecules. Analyses of the fractions that contained both capsid proteins and DNA (FIG. 3(a) fractions 2–4) demonstrated the presence of infectious units. The results taken together indicate the formation of capsid particles which contain supercoiled plasmid DNA and which are infective.

Proteins Present in Nuclear Extracts Assist in Packaging in vitro

SV40 assembly requires precise insertion of the carboxy-terminal arms of the VP1 molecules into the neighboring pentamers. However, an arm can easily insert, instead, into its own pentamer, thus interfering with assembly. To explain how such mistakes are avoided, the participation of chaperones has been invoked [Liddington, R. D, et al. (1991) ibid.]. The inventors rationalized that such chaperones may also be present in nuclear extracts of the Sf9 cells, and that they may facilitate capsid formation and entry of DNA into pre-formed aggregates. Indeed, experiments with crude nuclear extracts consistently yielded approximately 10 fold more infectious units than those performed with capsid aggregates which had been partially purified by glycerol gradients (Table 2). These results suggest that additional proteins present in the nuclear extract of Sf9 cells, presumably, chaperons, enhance DNA packaging in vitro. As chaperones require ATP for their activity we investigated whether the addition of ATP to the reaction improves packaging. Packaging was performed as above, in the presence of 5 mM ATP. The results shown in Table 1 suggest that ATP may indeed improve in vitro packaging, although the titers obtained in these experiments were lower than the usual.

The inventors have recently started to investigate whether the agnoprotein can also enhance DNA packaging in vitro. Nuclear extracts of Sf9 were prepared as described above from cells infected with the four recombinant baculoviruses expressing VP1, VP2 and VP3 and the agnoprotein, at moi 10 for each recombinant baculovirus. Packaging of DNA was performed after treatment of the nuclear extracts with DTT, as described above for the nuclear extract which contained the three capsid proteins. The results presented in Table 1, although inconclusive, suggest that the agnoprotein may improve packaging. The effect of the agnoprotein on packaging may be more critical when purified capsid proteins are used in the packaging reaction.

TABLE 1

The effect of ATP on in vitro packaging of pSO3cat

| | Infectious units/ml* | |
|---|---|---|
| Capsid proteins | No ATP added | + ATP |
| Nuclear extracts containing VP1 + VP2 + VP3 | $2.7 \times 10^3$ | $8 \times 10^3$ |
| Nuclear extracts containing VP1 + VP2 + VP3 + agnoprotein | $3.8 \times 10^3$ | $1.4 \times 10^4$ |

*titers after DNase I treatment

The Infections Particles Transmit Complete DNA Molecules which Are Biologically Functional The results shown in FIG. 2(c) may presumably reflect DNA which did not penetrate the cells but remained adsorbed on the cell surface, in structures which are DNase I resistant. To prove that the in vitro packaged DNA entered the cells, and that the DNA is biologically active in gene expression, the inventors asked whether the cat gene transmitted by pSO3cat expressed the CAT enzyme. CMT4 cells were harvested 3 days postinfection with in vitro packaged pSO3cat. CAT assays [Oppenheim et al. (1986) ibid] demonstrated enzyme activity at a significant level (FIG. 4(a)), although the moi in this experiment was very low (less than 1 IU×$10^4$ cells). These results indicate that the infectious units transmitted biologically active DNA into the target cells.

It was then to be verified whether complete DNA molecules became packaged in this experimental protocol. For production of SV40 virions, the complete SV40 molecule is required, including the regulatory region, and the early and the late genes. SV40 DNA was packaged as described above and used to infect CV-1 cells at a low moi (~1 IU/$10^4$ cells). After 2 weeks extensive cell lysis was visible, indicating that productive SV40 infection was going on (FIG. 4(b)). Only complete SV40 DNA, which can produce functional T-antigen as well as the late proteins, can produce virions on CV-1 cells. It was therefore concluded that the in vitro packaging system described herein produces particles which contain the complete circular DNA molecules.

In vitro Packaging Is Not Dependent on ses

A small DNA element, ses, is required for SV40 assembly in vivo. ses appears to play multiple roles in packaging. It is probably a recognition site for the capsid proteins, serving as a nucleation center in the initiations of viral assembly [Dalyot-Herman et al., ibid]. In addition, ses functions in regulating the late stages of the SV40 life cycle, in turning off viral gene activity and by allowing the capsid proteins to induce nucleosomal reorganization and chromatin condensation in the transition from replication and late transcription to packaging [Oppenheim el al. (1992) ibid.]. In vitro, the use of non-transcribing, naked plasmid DNA may be predicted to circumvent part of the requirements for ses. As shown in Tables 1 and 2, ses$^+$ (pSOγ-S) and ses$^-$ (pSOγ-N) plasmids are indeed packed in vitro at similar efficiencies, indicating that ses is dispensable for in vitro packaging. Possibly, in vitro packaging of SV40 pseudovirions may allow efficient transfer of human genes without any accessory viral DNA.

TABLE 2

Packaging with purified capsid proteins in comparison with total nuclear extracts of Sf9 cells infected with recombinant baculovirus.

| Capsid protein | Infectious units/ml | | | |
|---|---|---|---|---|
| | SV40 | pSO3cat | pSOγS | pSOγN |
| Nuclear extract containing VP1 + VP2 + VP3 | $1.5 \times 10^4$ | $4 \times 10^4$ | $7.5 \times 10^4$ | $9.5 \times 10^4$ |
| Purified$^a$ VP1 + VP2 + VP3 | $1.7 \times 10^3$ | $2.6 \times 10^3$ | $<1.7 \times 10^3$ | $1.6 \times 10^3$ |
| Nuclear extract containing VP1 | $7.5 \times 10^3$ | $5.3 \times 10^3$ | N.D. | N.D. |
| Purified$^a$ VP1 | $6.7 \times 10^3$ | $<1.7 \times 10^2$ | $<1.7 \times 10^2$ | $5 \times 10^2$ |
| Nuclear extract of uninfected SF9 cells | 0 | 0 | N.D. | N.D. |

$^a$partially purified by glycerol gradient

Plasmid Significantly Larger than SV40 Can Be Packaged in vitro

The genome size of SV40 plasmid is 5,243 bp, and the upper limit of plasmid packaging is ~5.4–5.7 kb [Chang, X. B. & Wilson, J. H. (1986) *J. Virol.* 58:393–401; Dalyot, N. (1994) Regulation of human globin genes and the development of a model for gene therapy of β-thalassemia, Ph.D. Thesis, The Hebrew University, Jerusalem]. SV40 DNA is packed in vivo as a minichromosome, complexed in nucleosomes, occupying large space within the virion particle [Martin, R. G. (1977) *Virology* 83:433–437]. Further experiments were performed under the same conditions as before, except that instead of SV40 or pSO3cat DNA other plasmids, significantly larger than SV40 size, were used. In each experiments, 1 μg of plasmid DNA was incubated with 2 μl of nuclear extracts of Sf9 cells infected with VP1+ VP2+VP3. The experiments were repeated at least twice for each plasmid. Typical results are shown in Table 3.

TABLE 3

In Vitro Packaging of Various Plasmid

| Plasmid units | Properties | Size(kb) | Infectious units/ml |
|---|---|---|---|
| SV40 | | 5.2 | $4.2 \times 10^4$ |
| pSO3cat | | 4.1 | $2.4 \times 10^4$ |
| pSOγ-S$^a$ | ses$^+$ | 4.3 | $7.5 \times 10^3$ |
| pSOγ-N$^a$ | ses$^-$ | 4.2 | $9.5 \times 10^3$ |
| pSO6β-1$^b$ | carries β-globin | 7.3 | $3.3 \times 10^4$ |
| pSO6β-5$^b$ | carries β-globin + LCR element | 7.4 | $1.2 \times 10^4$ |
| pSO6β-9$^b$ | carries β-globin + LCR element | 7.0 | $1.2 \times 10^4$ |
| pSM1$^c$ | carries MDR1 | 7.1 | $7.3 \times 10^3$ |

$^a$described in Oppenheim, A., ibid.
$^b$described in Dalyot, N., Ph.D Thesis (1996) The Hebrew University, Jerusalem
$^c$described in ,e.g., WO95/30762.

Importantly, the experiments demonstrated that various plasmids, carrying useful genes, can be packaged. Furthermore, packaging in vitro is not limited to 5.4–5.7 kb of plasmid DNA, and plasmids over 7 kb can be almost as efficiently packaged. This is presumably because under in vitro conditions naked DNA is packaged, rather than a minichromosome (which includes the DNA complexes in nucleosomes). The minichromosome occupies much more space, as compared to DNA of the same size, within the pseudoviral particle. It is also possible that in the absence of histones, the internal capsid proteins VP2 and VP3 assist in plasmid DNA condensation. The titers obtained in these experiments, around 1–5×$10^4$ IU/ml, are comparable to titers obtained by in vitro packaging of a number of currently used vectors.

In vitro packaging is probably accomplished by a mechanism which is different from the packaging in vivo. In the latter process, the viral capsid proteins are thought to assemble around the viral minichromosome, while in vitro, empty capsid-like structure (FIG. 1) serve as starting material. Furthermore, in vitro packaging utilizes naked DNA, prepared in *E. coli*. This result, combined with many of the inventors previous studies on in vivo packaging, leads to the prediction that potent regulatory sequences, such as β-globin LCR, which interfere with viral packaging in vivo [Chang et al. (1992) ibid; Dalyot et al. (1994) ibid.], will not interfere with in vitro packaging. It is hypothesized that the LCR elements interfere with in vivo packaging of SV40 pseudovirions by the formation of higher order nucleoprotein structures which is not compatible with chromatin condensation [Dalyot, N. (1994) ibid.]. The use of supercoiled plasmid DNA, in the absence of regulatory proteins which bind to these regulatory elements, is predicted to relieve this problem in vitro. Indeed, two LCR containing plasmids, pSO6β-5 and pSO6β-9, which are poorly packed in vivo (producing titers of $10^3$ and ~$10^4$ IU/ml, respectively [Dalyot, N. (1994) ibid.], yield here titers similar to pSO3cat (Table 3). The present results suggest that in vitro packaging will allow to combine in the constructs for gene therapy the optimal regulatory signal, which will lead to important improvement in expression of the delivered genes.

What is claimed is:

1. An infectious particle complex comprising semi-purified or pure SV40 VP1 capsid protein or a mixture of SV40 VP1 capsid protein and at least one other SV40 capsid protein; and a purified recombinant nucleic acid constituent packaged therein, wherein the nucleic acid constituent is selected from the group consisting of:
   (a) a purified exogenous naked DNA, or a purified exogenous naked DNA encoding an exogenous protein or peptide, or a purified exogenous naked DNA encoding RNA;

(b) a vector comprising any of the purified exogenous naked DNAs of (a);

(c) a purified exogenous RNA, or a purified exogenous RNA encoding an exogenous protein or peptide;

(d) a vector comprising any of the purified exogenous RNAs of (c); and (e) a purified exogenous antisense RNA, purified exogenous ribozyme RNA or a purified exogenous RNA or purified exogenous naked DNA which inhibits or prevents the expression of undesired protein or proteins in a mammalian cell;

and further comprising operatively linked elements sufficient for one or more of the following:

(i) replication of said constituent; or (ii) expression of said constituent; or in subcase (e)

(iii) prevention of expression of said undesired protein or proteins;

in said mammalian cell, wherein the recombinant nucleic acid packaged in the infectious particle complex is more infectious relative to unpackaged recombinant nucleic acid.

2. The complex according to claim 1, further comprising additional SV40 protein or proteins.

3. The complex according to claim 1, comprising a mixture of three semi-purified or pure SV40 capsid proteins.

4. The complex according to claim 1, wherein said other SV40 capsid protein is semi-purified or pure VP2 or VP3.

5. The complex according to claim 1, wherein said recombinant nucleic acid constituent is:

(a) purified exogenous circular or linear naked DNA;

(b) purified exogenous circular or linear naked DNA encoding a protein or peptide; or (c) purified exogenous circular or linear naked DNA encoding RNA.

6. The complex according to claim 5, wherein said purified exogenous circular or linear naked DNA is DNA which encodes a protein or peptide, wherein said protein or peptide is not made or contained in a mammalian cell prior to infection with the complex, or is purified exogenous naked DNA which encodes a protein or peptide, wherein said protein or peptide is made or contained in said cell in an amount insufficient for proper cell function prior to infection with the complex, or is purified exogenous naked DNA which encodes a protein or peptide, wherein said protein or peptide is made or contained in said cell in a form inadequate for proper cell function prior to infection with the complex, or encodes a RNA.

7. The complex according to claim 6, wherein said protein or peptide is an enzyme, a receptor, a structural protein, a regulatory protein or a hormone.

8. The complex according to claim 1, wherein said purified exogenous naked DNA further comprises a SV40 ori DNA sequence as a replication regulatory element and one or more regulatory elements sufficient for the expression of said exogenous RNA or exogenous protein or peptide in a mammalian cell.

9. The complex according to claim 1, wherein said constituent is purified exogenous RNA, wherein said purified exogenous RNA is RNA which encodes a protein or peptide which is not made or contained in a mammalian cell prior to infection with the complex, or is purified exogenous RNA which encodes a protein or peptide which is made or contained in said cell in an amount insufficient for proper cell function prior to infection with the complex, or is purified exogenous RNA which encodes a protein or peptide which is made or contained in said cell in a form, inadequate for proper cell function prior to infection with the complex, said purified exogenous RNA having regulatory elements, comprising a translation signal or signals sufficient for the translation of said protein or peptide in said mammalian cell, operatively linked thereto.

10. The complex according to claim 9, wherein said protein or peptide is an enzyme, a receptor, a structural protein, a regulatory protein or a hormone.

11. The complex according to claim 1, wherein said constituent encodes an exogenous protein or peptide which is, respectively, a protein or peptide which is not made or contained in a mammalian cell prior to infection with the complex, or is a protein or peptide which is made or contained in said cell in an amount insufficient for proper cell function prior to infection with the complex, or is a protein or peptide which is made or contained in said cell in a form inadequate for proper cell function prior to infection with the complex.

12. The complex according to claim 1, wherein said recombinant constituent is purified exogenous antisense RNA or naked DNA or purified exogenous ribozyme RNA, or any purified exogenous RNA or purified exogenous naked DNA which inhibits or prevents the expression of undesired protein or proteins in said mammalian cell.

13. The complex according to claim 1, wherein said cell is a human cell selected from the group consisting of hemopoietic cells, epithelial cells, endothelial cells, liver cells, epidermal cells, muscle cells, tumor cells, nerve cells and germ line cells.

14. The complex according to claim 13, wherein said hemopoietic cells are bone marrow cells, peripheral blood cells, or cord blood cells.

15. A method for the in vitro construction of the infectious particle complex of claim 1 comprising the following steps:

(a) allowing a semi-purified or pure SV40 VPI capsid protein or a mixture of VPI and at least one other SV40 capsid protein to self-assemble into SV40-like particles; and (b) bringing the SV40-like particles assembled in step (a) into contact with said purified recombinant nucleic acid constituent to give in vitro constructed viruses, or into contact with a vector of claim 1 to give pseudoviruses, so as to thereby effect in vitro construction of SV40 viruses or pseudoviruses.

16. A mammalian cell infected with the complex of claim 1.

17. The infected cell according to claim 16, wherein the cell is a human cell selected from the group consisting of hemopoietic cells, muscle cells, tumor cells, nerve cells and in vitro germ line cells.

18. An in vitro method of transforming a purified exogenous naked DNA, purified exogenous RNA, purified exogenous antisense RNA, purified exogenous ribozyme RNA into a cell comprising infecting said cell with the complex of claim 1.

19. A composition comprising an effective amount of the complex of claim 1 in a pharmaceutically-acceptable carrier.

20. A composition comprising an effective amount of the infected cells according to claim 16, in a pharmaceutically-acceptable carrier.

21. A complex comprising semi-purified or pure SV40 VPI capsid protein or a mixture of VPI and at least one other SV40 capsid protein, and a constituent, wherein the constituent is a purified exogenous protein or peptide.

22. The method of claim 15, wherein said in vitro constructed SV40 viruses or pseudoviruses are subjected to digestion by nuclease to remove non-packaged DNA.

23. The method according to claim 15, wherein in step (a) at least one other SV40 protein is added to the mixture of said SV40 capsid protein or proteins and said purified exogenous nucleic acid.

24. The method according to claim 15, wherein said exogenous nucleic acid is circular or linear naked DNA.

25. The method according to claim 15, wherein said exogenous nucleic acid is RNA.

26. The method according to claim 15, wherein said exogenous nucleic acid encodes a protein or peptide.

27. The method according to claim 24, wherein said circular or linear naked DNA is DNA which encodes a protein or peptide, wherein said protein or peptide is not made or contained in a mammalian cell prior to infection with said SV40 viruses or pseudoviruses, or is circular or linear naked DNA which encodes a protein or peptide, wherein said protein or peptide is made or contained in said cell in an amount insufficient for proper cell function prior to infection with said SV40 viruses or pseudoviruses, or is circular or linear naked DNA which encodes a protein or peptide, wherein said protein or peptide is made or contained in said cell in a form inadequate for proper cell function prior to infection with said SV40 viruses or pseudoviruses, or is circular or linear naked DNA which encodes RNA.

28. The method according to claim 27, wherein said circular or linear naked DNA encodes a protein or peptide which is an enzyme, a receptor, a structural protein, a regulatory protein or a hormone.

29. The method according to claim 15, wherein in step (b) the recombinant nucleic acid constituent further comprises an SV40 ori DNA sequence as a replication regulatory element and one or more regulatory elements sufficient for the expression of an exogenous protein encoded thereby in a cell.

30. The method according to claim 15, wherein said recombinant nucleic acid is purified exogenous RNA, wherein said purified exogenous RNA is RNA which encodes a protein or peptide, wherein said protein or peptide is not made or contained in a mammalian cell prior to infection with the complex, or is purified exogenous RNA which encodes a protein or peptide, wherein said protein or peptide is made or contained in an amount insufficient for proper cell function prior to infection with the complex, or is purified exogenous RNA which encodes a protein or peptide, wherein said protein or peptide is made or contained in said cell, in a form inadequate for proper cell function prior to infection with the complex, and wherein said purified exogenous RNA has regulatory elements, comprising a translation signal or signals sufficient for the translation of said protein in said mammalian cell, operatively linked thereto.

31. A method for the in vitro construction of SV40 viruses or pseudoviruses comprising a constituent, wherein the constituent comprises a purified exogenous protein or peptide, which method comprises the following steps:
   (a) allowing a semi-purified or purified SV40 VP1 capsid protein or a mixture of VP1 and at least one other SV40 capsid protein to self-assemble into SV40-like particles; and
   (b) bringing the SV40-like particles assembled in step (a) into contact with said purified exogenous protein, so as to thereby effect in vitro construction of SV40 viruses or pseudoviruses comprising said purified exogenous protein or peptide packaged therein.

32. The method according to claim 31, further comprising the step of purifying said SV40 viruses or pseudoviruses from any non-packaged exogenous protein or peptide.

33. The method according to claim 31, wherein said exogenous protein or peptide is a naturally occurring or recombinant protein or peptide, a chemically modified protein or peptide, or a synthetic protein or peptide.

34. The method according to claim 33, wherein said exogenous protein or peptide is a protein or peptide not made or contained in a cell prior to infection with the complex, or is a protein or peptide made or contained in said cell in an amount insufficient for proper cell function prior to infection with the complex, or is a protein or peptide made or contained in said cell in a form inadequate for proper cell function prior to infection with the complex.

35. The method according to claim 34, wherein said cell is a human cell selected from the group consisting of hemopoietic cells, muscle cells, tumor cells, nerve cells and germ line cells.

36. The method according to claim 35, wherein said hemopoietic cells are bone marrow cells, peripheral blood cells, cord blood cells, or liver cells.

37. A method for the in vitro construction of SV40 pseudoviruses comprising a recombinant nucleic acid constituent wherein said recombinant constituent comprises purified exogenous antisense RNA, or purified exogenous ribozyme RNA or purified exogenous RNA or purified exogenous recombinant naked DNA which inhibits or prevents the expression of undesired protein or proteins in a mammalian cell, comprising the following steps:
   (a) allowing a semi-purified or pure SV40 VP1 capsid protein or a mixture of VP1 and at least one other SV40 capsid protein to self assemble into SV40-like particles; and
   (b) bringing said SV40-like particles obtained in step (a) into contact with said purified exogenous antisense RNA, or purified exogenous ribozyme RNA, or purified exogenous RNA or purified exogenous recombinant naked DNA which inhibits or prevents the expression of undesired proteins in a mammalian cell,
so as to thereby effect in vitro construction of SV40 pseudoviruses.

38. The method of claim 37, further comprising the step of subjecting said pseudoviruses to digestion by nuclease to remove non-packaged DNA.

39. The method according to claim 37, wherein in step (a) at least one other SV40 protein is added to the semi-purified or pure SV40 VPI capsid protein or the mixture of VPI and at least one other SV40 capsid protein.

40. The complex of claim 2, further comprising SV40 agnoprotein.

41. The method of claim 23, wherein the at least one other SV40 protein is agnoprotein.

42. The method of claim 39, wherein the at least one other SV40 protein is agnoprotein.

* * * * *